US008332159B2

(12) United States Patent
Murakami et al.

(10) Patent No.: US 8,332,159 B2
(45) Date of Patent: Dec. 11, 2012

(54) METHOD FOR ENHANCING EFFICACY OF PREPARATION OF MONOCLONAL ANTIBODY

(75) Inventors: Toshio Murakami, Kikuchi (JP); Hirofumi Higuchi, Kikuchi (JP); Keiichi Makizumi, Kikuchi (JP); Toshihiro Maeda, Kikuchi (JP); Hiroshi Mizokami, Kikuchi (JP)

(73) Assignee: Juridical Foundation The Chemo-Sero-Therapeutic Research Institute, Kumamoto-Ken (JP)

( * ) Notice: Subject to any disclaimer, the term of this patent is extended or adjusted under 35 U.S.C. 154(b) by 291 days.

(21) Appl. No.: 10/546,293

(22) PCT Filed: Feb. 18, 2004

(86) PCT No.: PCT/JP2004/001822
§ 371 (c)(1),
(2), (4) Date: Aug. 22, 2005

(87) PCT Pub. No.: WO2004/074516
PCT Pub. Date: Sep. 2, 2004

(65) Prior Publication Data
US 2006/0280751 A1 Dec. 14, 2006

(30) Foreign Application Priority Data
Feb. 20, 2003 (JP) .................................. 2003-042819

(51) Int. Cl.
*G06F 7/00* (2006.01)
(52) U.S. Cl. .............. 702/20; 702/19; 703/11; 707/700; 424/184.1
(58) Field of Classification Search .................... None
See application file for complete search history.

(56) References Cited

U.S. PATENT DOCUMENTS

| 5,712,373 A | 1/1998 | Eda et al. |
| 5,858,369 A | 1/1999 | Matsuo et al. |
| 6,114,143 A | 9/2000 | Eda et al. |
| 6,447,778 B1 | 9/2002 | Rubinstein et al. |
| 6,827,939 B2 | 12/2004 | Fujii et al. |

FOREIGN PATENT DOCUMENTS

| EP | 690 132 | 1/1996 |
| JP | 06-217791 | 8/1994 |
| JP | 10-182489 | 7/1998 |
| JP | 2001-192399 | 7/2001 |
| WO | WO 90/15078 | 12/1990 |
| WO | 93/19785 | 10/1993 |
| WO | 02/059154 A2 | 8/2002 |

OTHER PUBLICATIONS

Di Leo, A. et al., "Current Status of HER2 Testing", Oncology, (2002), vol. 63, Suppl. 1, pp. 25-32.
Geysen, H. M. et al., :Use of peptide synthesis to probe viral antigens for epitopes to a resolution of a single amino acid, Proc. Natl. Acad. Sci. USA, (1984), vol. 81, pp. 3998-4002.
Matsushita, S. et al., "Characterization of a Human Immunodeficiency Virus Neutralizing Monoclonal Antibody and Mapping of the Neutralizing Epitope", Journal of Virology, (1988), vol. 62, No. 2, pp. 2107-2114.
Okamoto, Y. et al., "In SCID-hu Mice, Passice Transfer of a Humanized Antibody Prevents Infection and Atrophic Change of Medulla in Human Thymic Implant due to Intravenous Inoculation of Primary HIV-1 Isolate", The Journal of Immunology, (1998), vol. 160, pp. 69-76.
Watanabe, T. et al., "Genetic testing for effective Herceptin therapy", Nippon Rinsho, (2002), vol. 60, No. 3, pp. 603-611.
Shibata et al; "A Role of Mutations in Non-V3 Envelope Regions for Escape from a Broad Neutralizing Anti-V3 Monoclonal Antibody, KD-247, during in vitro Selection"; *13 Conference on Retroviruses and Opportunistic Infections*; Retrieved from the internet: URL:/http://www.retroconference.org/2006/Abstracts/26741.htm>, 2006.
Tugarinov et al; "NMR structure of an anti-gp120 antibody complex with a V3 peptide reveals a surface important for co-receptor binding." *Structure with Folding and Design*, vol. 8, No. 4, pp. 385-395, 2000.
Wang Feng-Xiang et al; Emergence of autologous neutralization-resistant variants from preexisting human immunodeficiency virus (HIV) quasi species during virus rebound in HIV type 1-infected patients undergoing highly active antiretroviral therapy; *The Journal of Infectious Diseases*; vol. 185, No. 5, pp. 608-617, 2002.
Zvi et al; The principal neutralizing determinant of HIV-1 located in V3 of gp120 forms of a 12-residue loop by internal hydrophobic interactions; *FEBS Letters*, vol. 368, No. 2. pp. 267-270, 1995.
Japanese-language Office Action dated Mar. 30, 2010, issued in corresponding Japanese patent application.

*Primary Examiner* — Mary Zeman
(74) *Attorney, Agent, or Firm* — Browdy and Neimark, P.L.L.C.

(57) ABSTRACT

A method of enhancing the efficacy of a monoclonal antibody preparation wherein antigens from patients are tested for their reactivity with the antibody. An amino acid sequence of an expressed protein is deuced from a nucleotide sequence determined by isolation and analysis of a target molecule gene in a biopsy from a patient. This is compared with the previously determined amino acid sequence recognized by the monoclonal antibody preparation in order to assess the fitness of patients for administration of the monoclonal antibody preparation.

3 Claims, 6 Drawing Sheets

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
acacatggaa ttaggccagt                                                 20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaattcccct ccacaattaa                                                 20

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gccggatcct caactcaact gctgttaaat                                      30

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
gctctgcagt caaatttctg ggtcccctcc tgagg                                35

<210> SEQ ID NO 5
```

```
<211> LENGTH: 7
<212> TYPE: PRT
<213> ORGANISM: HIV-1

<400> SEQUENCE: 5

Ile Gly Pro Ala Arg Ala Phe
 1               5

<210> SEQ ID NO 6
<211> LENGTH: 7
<212> TYPE: PRT
<213> ORGANISM: HIV-1

<400> SEQUENCE: 6

Ile Gly Pro Gly Arg Ser Phe
 1               5

<210> SEQ ID NO 7
<211> LENGTH: 7
<212> TYPE: PRT
<213> ORGANISM: HIV-1

<400> SEQUENCE: 7

Ile Gly Pro Gly Arg Ala Leu
 1               5

<210> SEQ ID NO 8
<211> LENGTH: 7
<212> TYPE: PRT
<213> ORGANISM: HIV-1

<400> SEQUENCE: 8

Ile Gly Pro Gly Arg Thr Phe
 1               5

<210> SEQ ID NO 9
<211> LENGTH: 7
<212> TYPE: PRT
<213> ORGANISM: HIV-1

<400> SEQUENCE: 9

Ile Gly Pro Gly Arg Ala Ile
 1               5

<210> SEQ ID NO 10
<211> LENGTH: 7
<212> TYPE: PRT
<213> ORGANISM: HIV-1

<400> SEQUENCE: 10

Val Gly Pro Gly Arg Ala Leu
 1               5

<210> SEQ ID NO 11
<211> LENGTH: 7
<212> TYPE: PRT
<213> ORGANISM: HIV-1

<400> SEQUENCE: 11

Ile Gly Pro Gly Arg Ala Phe
 1               5
```

METHOD FOR ENHANCING EFFICACY OF PREPARATION OF MONOCLONAL ANTIBODY

TECHNICAL FIELD

The present invention belongs to the technical field of medicaments. More specifically, the present invention relates to a method for enhancing efficacy of a preparation of a monoclonal antibody, said method being carried out for selecting patients who possess an antigen recognized by said monoclonal antibody.

BACKGROUND ART

In recent years, for clinical application of a monoclonal antibody, a therapy with administration of a monoclonal antibody preparation has been developed. A monoclonal antibody preparation may effectively be used through interaction between a monoclonal antibody and an antigen occurring within the living body. Thus, efficacy of a monoclonal antibody preparation may be enhanced if an expression level of said antigen is previously tested to select subjects to be applied with said preparation. A monoclonal antibody may be advantageous from the viewpoint of safety and efficacy due to its extremely high specificity. However, in case that diversity occurs in an amino acid sequence of an antigenic epitope region, a monoclonal antibody will become less reactive with an antigen and hence its effectiveness may be deteriorated. Therefore, for use of a monoclonal antibody preparation as a medicament, it will be a useful means for enhancing efficacy of said monoclonal antibody preparation not only to test previously an expression level of an antigen within the living body but also to confirm diversity of an antigen and to select subjects for administration.

Among monoclonal antibody preparations wherein subjects to be administered therewith are tested and selected is anti-HER2 monoclonal antibody (Trastuzumab) now commercially available. Trastuzumab is a monoclonal antibody to HER2 protein that is overexpressed in about 20 to 30% of breast cancer patients. For clinical test for selecting subjects to be administered with anti-HER2 monoclonal antibody, Southern blot or Furuorescent in situ hybridization (FISH) technique for DNA amplification of HER2/neu gene; Northern blot or reverse transcription polymerase chain reaction (RT-PCR) technique for screening overexpression of HER2 mRNA; or Western blot, ELISA or immunohistochemistry technique for screening overexpression of HER2 protein have been attempted. With these tests, efficacy of Trastuzumab has been enhanced in cases of HER2 overexpression, suggesting that in therapy with a monoclonal antibody preparation selecting previously subjects to be administered with said preparation is useful for enhancing efficacy of the monoclonal antibody preparation (e.g. Nippon Rinsho, Vol. 60, No. 3 (2002)).

DISCLOSURE OF THE INVENTION

Technical Problems to be Solved by the Invention

On the other hand, in case that there occurs diversity in an amino acid sequence of an epitope region to thereby alter affinity of antigen-antibody reaction, efficacy of an antibody preparation is estimated to be lowered as a consequence of antigenic diversity, prediction of which is of great significance from clinical point of view. For this purpose, testing an expression level of an antigenic protein alone as in Trastuzumab is insufficient and a newly established test method will be necessary. This is because, even if a certain antigen is highly expressed as a protein and is detectable quantitatively, said antigen must be assessed as being unfit if it exhibits diversity in an amino acid sequence of an epitope in wild type recognized by a monoclonal antibody and there are multiplicity of antigenic variants with lowered reactivity with said monoclonal antibody. Accordingly, when there exists diversity in an amino acid sequence of an epitope of a certain antigen, an extent of reactivity of an antibody to each of epitopes with different amino acid sequences needs be directly confirmed through antigen-antibody reaction. However, in order to distinguish antigenic molecules with different amino acid sequences of an epitope region from each other among antigens that may occur in extremely small quantities and to capture and detect said molecules with an antibody, a higher sensitivity will be required. It is also difficult to distinguishably detect an expression level of an antigen on one hand and reactivity of an antibody on the other hand.

From the viewpoints mentioned above, for a monoclonal antibody preparation wherein an antigen to which a monoclonal antibody is directed is a protein with diversity in an amino acid sequence of an epitope recognized by said monoclonal antibody, development of a test method with high sensitivity and rapidity is desired for selection of subjects to be administered with said preparation.

Means to Solve the Problems

The present invention relates to a method for enhancing efficacy of a monoclonal antibody preparation when said monoclonal antibody preparation is administered to patients, wherein said method comprises selecting patients to be administered with said monoclonal antibody preparation by previously analyzing an amino acid sequence of an antigenic protein of a target molecule present in patients before administration of said monoclonal antibody preparation.

The present invention further relates to the method for enhancing efficacy of a monoclonal antibody preparation as mentioned above wherein said method comprises steps: (1) deducing an amino acid sequence of a protein expressed in patients from a nucleotide sequence of a gene of a target molecule determined by isolation and analysis of said gene in biopsy from patients; (2) assessing fitness of patients for administration of said monoclonal antibody preparation by comparing the amino acid sequence deduced in step (1) with an amino acid sequence that is recognizable by said monoclonal antibody as previously determined (hereinafter referred to as "reference sequence"); and (3) selecting patients to be administered with said monoclonal antibody preparation with its expected efficacy based on the fitness assessed in step (2).

Diversity in an amino acid sequence of an antigenic epitope recognized by a monoclonal antibody preparation may alter binding affinity of the antibody to the antigen. In case of an antigen that exhibits a genetic polymorphism in an epitope region, the present inventors had the view that, in place of a direct measurement of binding of a monoclonal antibody through immunochemical detection, diversity of an antigen expressed in patients may be analyzed based on analysis of its nucleotide sequence to thereby predict binding between said antigen and said antibody. Thus, for a monoclonal antibody in which correlation was found between an amino acid sequence of an epitope and reactivity of antigen/antibody, data of such correlation were collected. With the data thus obtained was then compared a nucleotide sequence of an epitope region of an antigen from patients to allow for efficient selection of patients to be administered with a monoclonal antibody preparation to complete a method in accordance with the present invention.

With the progress of PCR and nucleotide sequence analysis techniques, the method in accordance with the present invention may be performed with a high sensitivity in a wide use and allows for direct analysis without cloning of DNAs among which their variants are present. Therefore, in accordance with the present invention, prediction of efficacy of a monoclonal antibody preparation now becomes possible by merely determining a nucleotide sequence encoding an epitope region of an antigen of an expressed protein without need of actually measuring binding affinity between said antigen and said monoclonal antibody.

More Efficacious Effects than Prior Art

In accordance with the present invention, a method for enhancing overall efficacy of a monoclonal antibody preparation when said monoclonal antibody preparation is administered to patients is provided, without actually measuring binding affinity between an antigen of an expressed target protein and said monoclonal antibody through isolation and purification of said antigen, by selecting patients to be administered with said monoclonal antibody preparation by previously analyzing a nucleotide sequence that encodes an epitope region of said antigen and by comparing said sequence with an amino acid sequence that is recognizable by said monoclonal antibody as previously determined ("reference sequence") to thereby assess fitness of patients for administration of said monoclonal antibody preparation.

BRIEF DESCRIPTION OF DRAWINGS

FIG. 2 is a graph showing binding of KD-247 and each of synthetic peptides wherein each of the amino acid residues from the N-terminal "I" to the C-terminal "Y" in the synthetic peptide "IHIGPGRAFY" (SEQ ID NO:12), which is the PND region of the laboratory strain of HIV-1 (MN strain) proved to be neutralized by KD-247, was replaced with the other 19 naturally occurring amino acid residues as shown in FIG. 2*a* to FIG. 2*j*, respectively, for investigation of versatility of the amino acid sequence recognized by the monoclonal antibody. In FIG. 2*a* to FIG. 2*j*, the bar with a slanting line indicates no alteration of the original amino acid residue.

FIG. 3 is a graph showing binding of KD-247 to an amino acid sequence at the middle portion of V3 region of a protein expressed from an amplified HIV-1 gene V3 region from patients, for investigation of the amino acid sequence recognized by the monoclonal antibody with expressed protein, wherein the binding is presented as a relative binding activity relative to the binding to a protein expressed from the gene from MN strain (100%). Horizontal lines indicate mean values for each of the amino acid sequences. In FIG. 3, "1" to "33" are expressed proteins having the following sequences in the middle portion of V3 region: 1: IAPGRAF (SEQ ID NO:22); 2: IAPGRAL (SEQ ID NO:23); 3: IAPGSAF (SEQ ID NO:24); 4: IGPGRAF (SEQ ID NO:25); 5: IGPARAF (SEQ ID NO:26); 6: IGPGGAF (SEQ ID NO:27); 7: IGPGKAF (SEQ ID NO:28); 8: IGPGRAF (SEQ ID NO:29); 9: IGPGRAI (SEQ ID NO:30); 10: IGPGRAL (SEQ ID NO:31); 11: IGPGRAS (SEQ ID NO:32); 12: IGPGRAV (SEQ ID NO:33); 13: IGPGRAW (SEQ ID NO:34); 14: IGPGRAY (SEQ ID NO:35); 15: IGPGRPF (SEQ ID NO:36); 16: IGPGRRF (SEQ ID NO:37); 17: IGPGRSF (SEQ ID NO:38); 18: IGPGRSV (SEQ ID NO:39); 19: IGPGRTF (SEQ ID NO:40); 20: IGPGRTL (SEQ ID NO:41); 21: IGPGRTV (SEQ ID NO:42); 22: IGPGRVF (SEQ ID NO:43); 23: IGPGRVY (SEQ ID NO:44); 24: IGPGSAF (SEQ ID NO:45); 25: IGSGRAF (SEQ ID NO:46); 26: LGPGGAF (SEQ ID NO:47); 27: LGPGRAF (SEQ ID NO:48); 28: MGPGGAF (SEQ ID NO:49); 29: MGPGKAF (SEQ ID NO:50); 30: MGPGRAF (SEQ ID NO:51); 31: MGPGRVY (SEQ ID NO:52); 32: VGPGRAL (SEQ ID NO:53); 33: VGPGRAV (SEQ ID NO:54).

BEST MODE FOR CARRYING OUT THE INVENTION

In accordance with the method of the present invention, for assessing fitness of patients for administration of a monoclonal antibody preparation and selecting patients to be administered with said monoclonal antibody preparation with its expected efficacy, it is indispensable to compare an amino acid sequence of a target molecule from patients with a previously determined "reference sequence". The term "reference sequence" as used herein refers to an amino acid sequence of an epitope region of an antigen, which amino acid sequence a monoclonal antibody as an active ingredient of a monoclonal antibody preparation to be administered may recognize and bind to. After such an amino acid sequence of an epitope region is determined as "reference sequence", correlation between efficacy (e.g. neutralizing activity) of said monoclonal antibody and "reference sequence" may be investigated. In case that diversity is seen in an amino acid sequence of an epitope region, e.g. human immuno-deficiency virus type 1 (HIV-1), a universal sequence commonly shared among diverse amino acid sequences of said epitope region is determined as "reference sequence".

As such, by previously determining an amino acid sequence of an epitope region recognized and bound by a monoclonal antibody as an active ingredient of a monoclonal antibody preparation, and by determining an amino acid sequence to which said monoclonal antibody may manifest its efficacy as "reference sequence", assessment of fitness of patients for administration of said monoclonal antibody preparation becomes possible through comparison with said "reference sequence".

For the purpose of the present invention, (1) analysis of an amino acid sequence ("reference sequence") of an epitope region recognized by a monoclonal antibody; (2) analysis of a nucleotide sequence that encodes a region encompassing an epitope region of a target molecule present in a biopsy from patients; and (3) acquisition of data concerning correlation between diversity in an amino acid sequence of an antigenic protein and a potency of a monoclonal antibody, need previously be performed.

Specifically, the present invention may be performed in the following processes. For a typical antigen recognized by a monoclonal antibody of interest, binding of said monoclonal antibody to peptide fragments consisted of a protein is investigated to identify an epitope region of said antigen. The peptide fragments may be prepared by digestion of an antigenic protein with a proteolytic enzyme or chemical synthesis of the peptide fragments based on known amino acid sequence information. Analysis of reactivity of said peptide fragments and a monoclonal antibody includes an immunochemical method such as ELISA and dot blot as well as a method using surface plasmon resonance biosensor. Antigens present within the living body include those of exogenous origin such as viruses, bacteria and toxins and of endogenous origin such as cancer specific antigens and disease-related molecules.

For determining a nucleotide sequence of said epitope region in an antigenic protein present within the living body of patients, a region that flanks said epitope region and has scarcely any variance in an amino acid sequence is selected and based on a nucleotide sequence of said region primers for amplification of a nucleic acid are designed. For analysis of a nucleotide sequence of the epitope region of said antigen, using a biological sample such as blood or a tissue, a DNA encoding the epitope region is amplified by PCR using as a template a cDNA obtained from RNAs with a reverse transcriptase or a DNA as well as said primers. The amplified DNAs are sequenced directly or after cloning with a DNA sequencer.

Reactivity of a monoclonal antibody to an antigen having a variety of amino acid sequences in an epitope region may be determined by cloning a DNA obtained as described above containing an epitope region and then measuring binding of said monoclonal antibody to a protein which is expressed in E. coli from the cloned DNA. Furthermore, correlation between an amino acid sequence of said epitope region and efficacy of said monoclonal antibody may be confirmed not only by an antigen-binding activity but also by in vitro, ex vivo or in vivo test using as an index an anti-viral activity or an anti-tumor activity. For example, virus derived from patients is cloned so that an amino acid sequence of said epitope region may be determined from its nucleotide sequence and simultaneously a viral neutralizing activity is measured to thereby provide data of correlation between the amino acid sequence of said epitope region and efficacy of said monoclonal antibody.

A typical example of viruses where diversity in an antigen may be seen is human immunodeficiency virus type 1 (HIV-1). Principal neutralizing domain (PND) of HIV-1 is localized at the middle portion of the 3rd variable region (V3 region) of the envelope glycoprotein gp120. The present inventors have prepared a humanized monoclonal antibody to PND and formulated said antibody for clinical application. Said monoclonal antibody was affected for its neutralizing activity to HIV-1, i.e. binding to an antigen of HIV-1, due to variance in an amino acid sequence of PND region. Thus, for clinical application of said antibody, it was estimated that analysis of an amino acid sequence of the epitope region and subsequent selection of subjects to be administered with said antibody will lead to enhancement of efficacy of said antibody.

As such, in order to first confirm the presence of an antigen to which said monoclonal antibody is capable of binding, correlation between an amino acid sequence of an epitope region and binding of said monoclonal antibody to the epitope region was investigated to determine the amino acid sequence recognized by said monoclonal antibody with its efficacy being expected by the following processes:
(1) Using synthetic peptide fragments consisting of the sequence of PND region, an epitope region sequence recognized by said monoclonal antibody was confirmed.
(2) A V3 region gene was amplified and cloned from a virus isolated from patients and expressed as a fusion protein with β-galactosidase. A binding of said monoclonal antibody to the expressed protein of said V3 region was determined and correlation between the amino acid sequence of the epitope region and binding of said monoclonal antibody was investigated.
(3) Based on the thus obtained results, candidate "reference sequence" of said monoclonal antibody was selected.
(4) A neutralizing activity of said monoclonal antibody to HIV-1 was determined to confirm that correlation exists between the "reference sequence" described above and the neutralizing activity.

(5) HIV-1 V3 region genes were amplified from plasma or peripheral mononuclear cells from patients and their nucleotide sequences were determined. Amino acid sequences were deduced from the obtained nucleotide sequences and compared with the "reference sequence" described above in order to predict fitness of the patients of interest to said monoclonal antibody.

Based on the findings as described above, it was found that diversity of an antigen expressed in patients may be analyzed on the basis of a nucleotide sequence so as to predict binding of said antigen and an antibody to said antigen. For use in clinical scenes, in case that HIV-1 is a target molecule for instance, a method for selecting subjects to be administered with a monoclonal antibody preparation is provided using plasma from patients as a sample by the processes as described below.

HIV-1 RNAs in plasma are converted to DNAs with a reverse transcriptase and amplification of the nucleic acid of V3 region is performed. The amplified DNA fragments, directly or after cloning, are analyzed for their nucleotide sequences. Amino acid sequences are then deduced from the obtained nucleotide sequences and compared with the previously selected "reference sequence" of the amino acid sequence that is recognizable by the monoclonal antibody in said monoclonal antibody preparation. The "reference sequence" may be determined by measuring binding to peptides or expressed proteins or HIV-1 neutralizing activity of said monoclonal antibody as described above. Besides, by analyzing correlation between the amino acid sequence of PND region of HIV-1 from patients and efficacy of said monoclonal antibody preparation through clinical tests, more particular data of "reference sequence" may be obtained.

The present invention is explained in more detail by means of the following Examples but should not be construed to be limited thereto.

Example 1

Analysis of Amino Acid Sequence Recognized by Anti-HIV Monoclonal Antibody Using Synthetic Peptides An amino acid sequence recognized by KD-247, a humanized monoclonal antibody to PND region, was analyzed using synthetic peptides derived from the middle portion of V3 region of HIV-1 gp120. Peptides were synthesized by Pepscan technique (Geysen, H. M. et al., Proc. Natl. Acad. Sci. USA, 81, 3998-4002, (1984)) and binding activity of KD-247 to these peptides was determined by ELISA. In order to determine the shortest amino acid sequence that is recognizable by KD-247, a peptide of the ten amino acid residues "IHIGPGRAFY" (SEQ ID NO:12), which is the amino acid sequence of the middle portion of V3 region of laboratory HIV-1 strain (MN strain) that is neutralized by KD-247, and peptides wherein amino acid residues were sequentially deleted one by one from the above peptide "IHIGPGRAFY" (SEQ ID NO:12) to the extent of peptides with four amino acid residues in length were synthesized as follows: "IHIGPGRAF"(SEQ ID NO:13), "HIGPGRAFY"(SEQ ID NO:14), "IHIGPGRA"(SEQ ID NO:55), "HIGPGRAF" (SEQ ID NO:15), "IGPGRAFY"(SEQ ID NO:16), "IHIGPGR"(SEQ ID NO:56), "HIGPGRA"(SEQ ID NO:57), "IGPGRAF"(SEQ ID NO:11), "GPGRAFY"(SEQ ID NO:58), "IHIGPG"(SEQ ID NO:59), "HIGPGR"(SEQ ID NO:18), "IGPGRA"(SEQ ID NO:19), "GPGRAF"(SEQ ID NO:20), "PGRAFY"(SEQ ID NO:60), "IHIGP"(SEQ ID NO:61), "HIGPG"(SEQ ID NO:62), "IGPGR"(SEQ ID NO:21), "GPGRA"(SEQ ID NO:63), "PGRAF"(SEQ ID NO:64), "GRAFY"(SEQ ID NO:65), "IHIG"(SEQ ID NO:66), "HIGP"(SEQ ID NO:67), "IGPG"(SEQ ID NO:68), "GPGR"(SEQ ID NO:69), "PGRA"(SEQ ID NO:70), "GRAF"(SEQ ID NO:71), and "RAFY"(SEQ ID NO:72).

Figure 1:
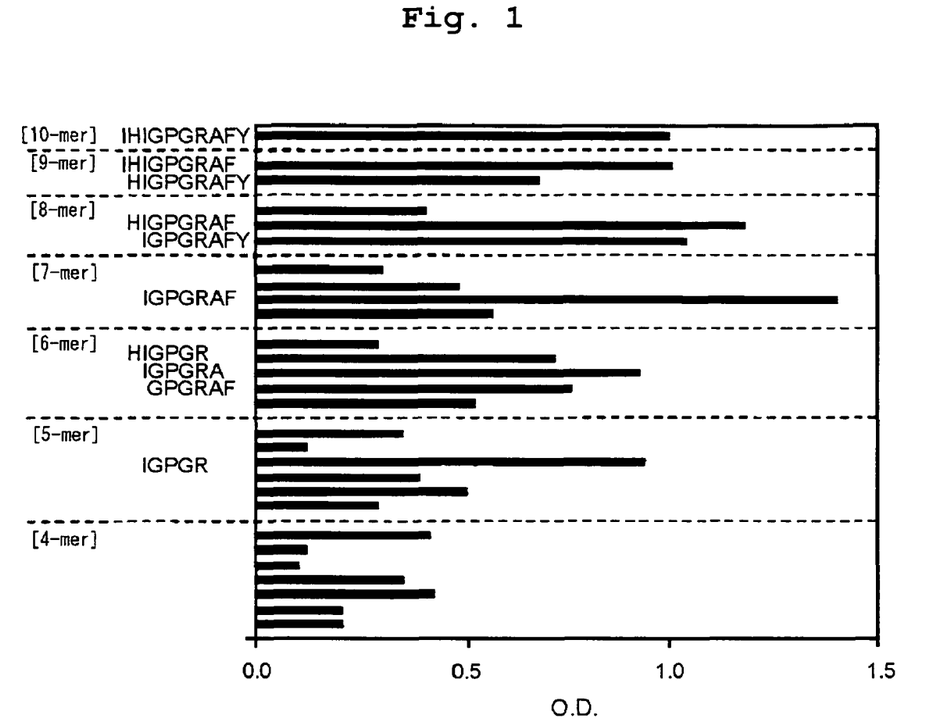
FIG. 1 is a graph showing binding of KD-247 and each of synthetic peptides wherein amino acid residues are sequentially deleted one by one from the synthetic peptide "IHIGPGRAFY" (SEQ ID NOS:12-21), which is the PND region of the laboratory strain of HIV-1 (MN strain) proved to be neutralized by KD-247, for investigation of a site recognized by the monoclonal antibody.
Figure 2A:
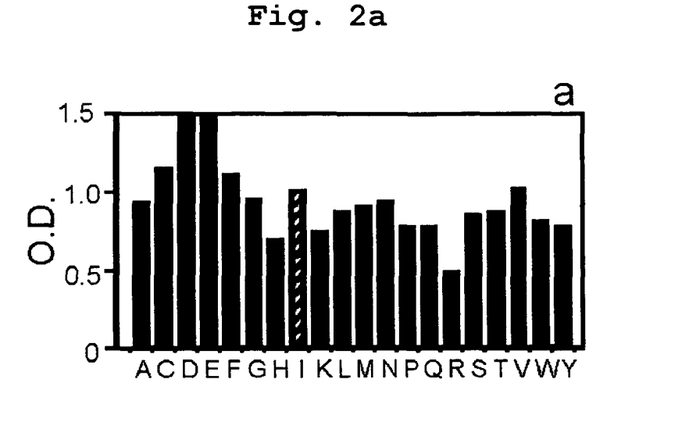
Figure 2B:
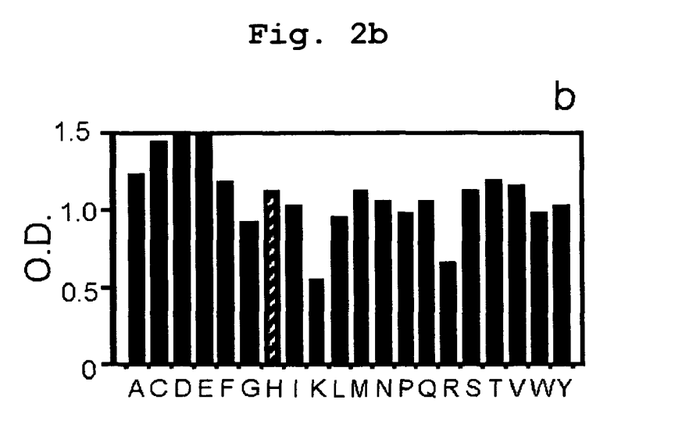
Figure 2C:
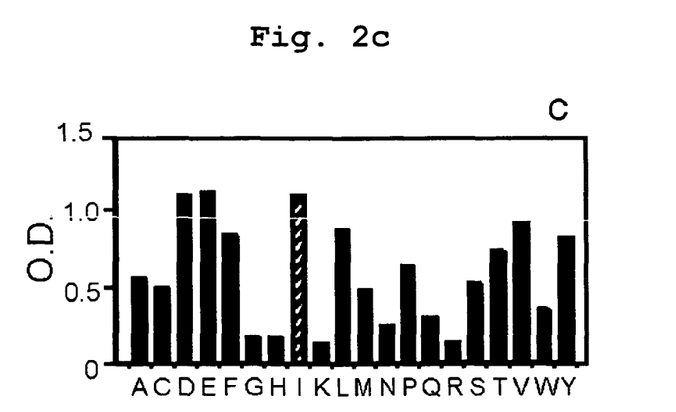
Figure 2D:
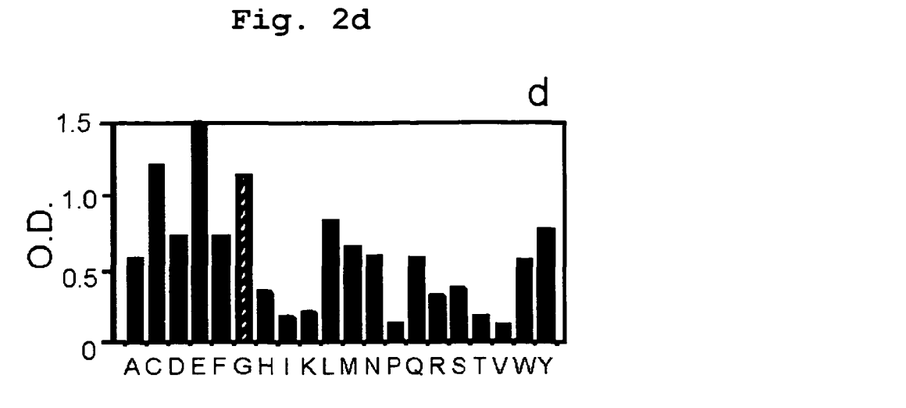
Figure 2E:
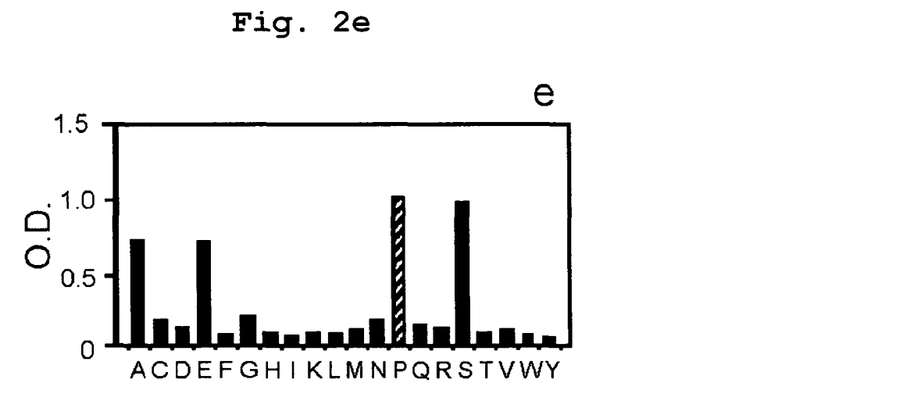
Figure 2F:
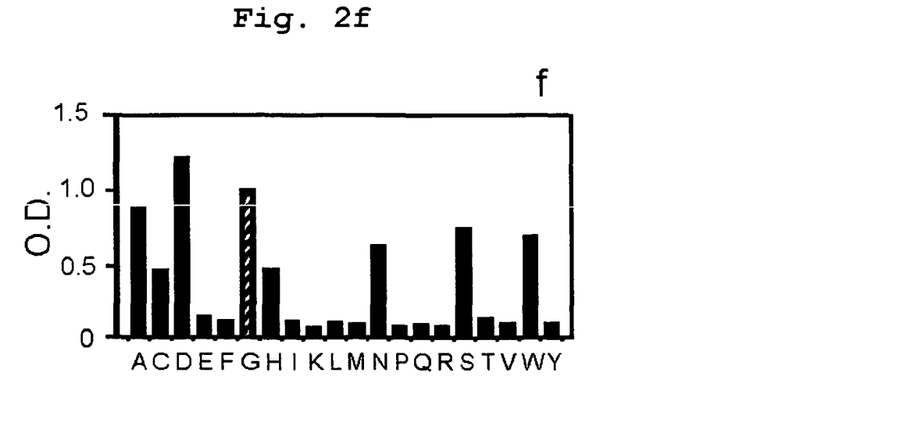
Figure 2G:
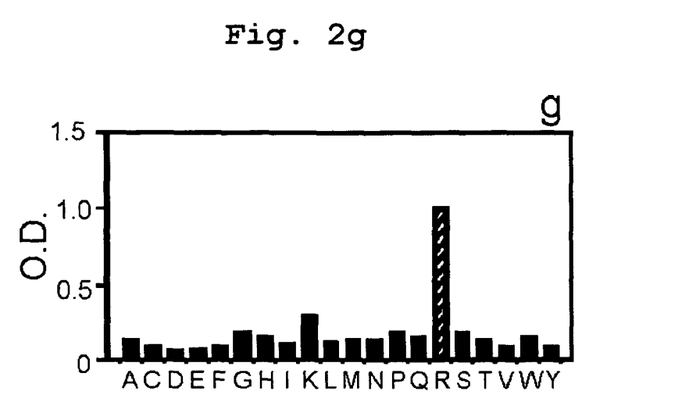
Figure 2H:
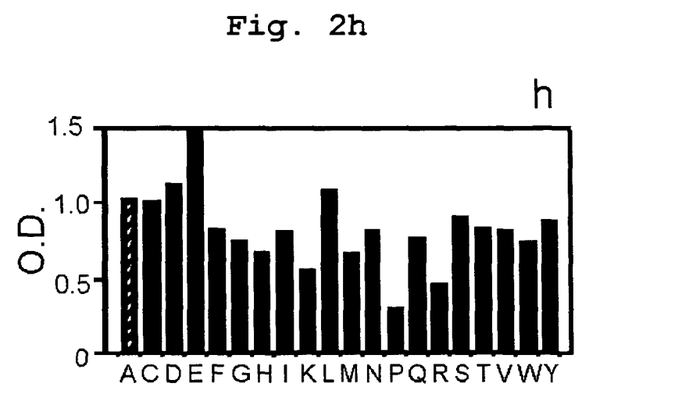
Figure 2I:
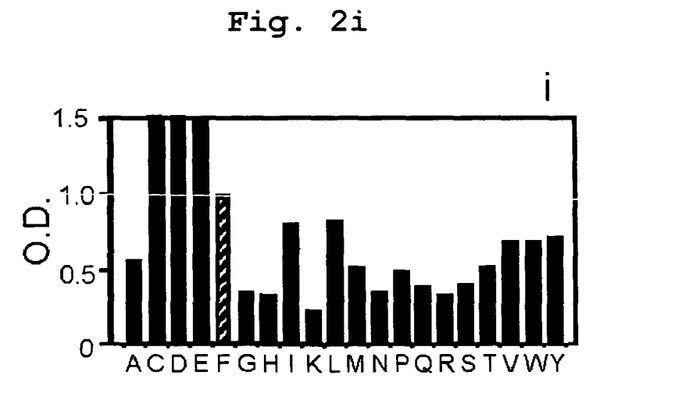
Figure 2J:
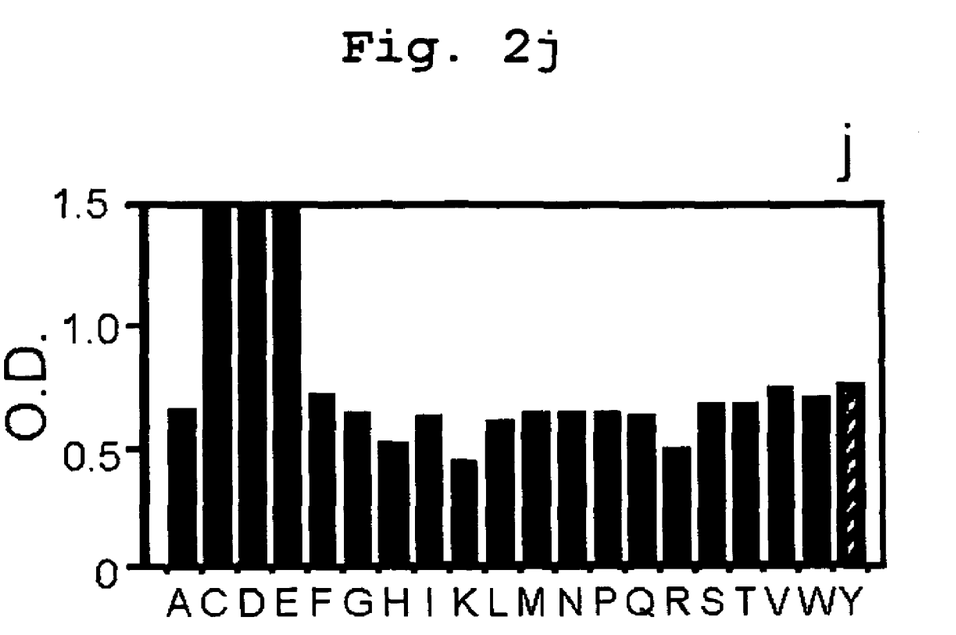
Figure 3:
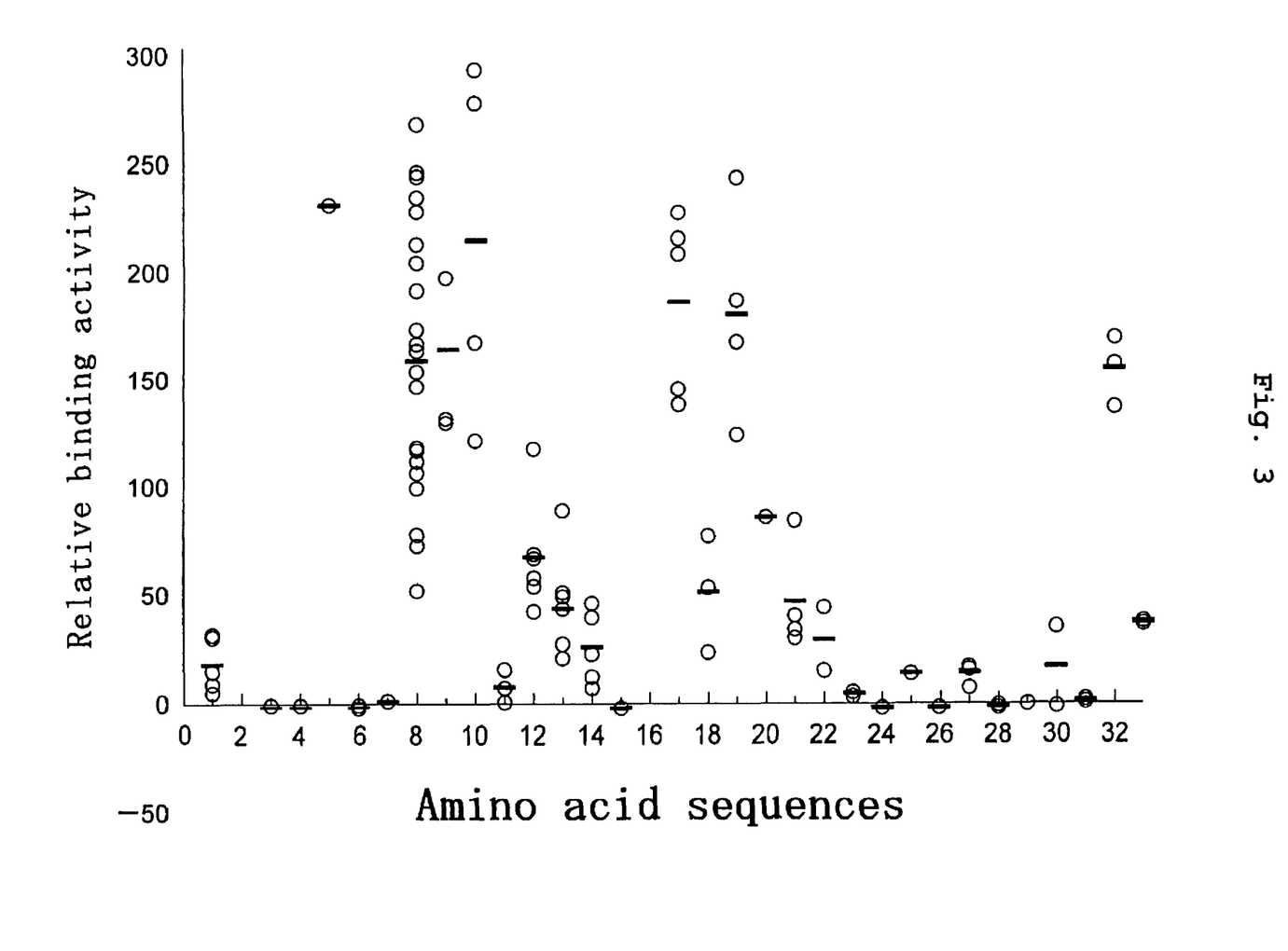

Polyethylene rods bound with the synthetic peptides were precoated with a phosphate buffered saline containing 2% bovine serum albumin and 0.1% Tween 20 and reacted with 2 μg/ml of KD-247. KD-247 bound with the peptides was measured with peroxidase-labeled anti-human κ antibody and the substrate. As shown in FIG. 1, the shortest amino acid sequence was found to be "IGPGR".

In order to investigate if reactivity of KD-247 may be altered when each of the amino acid residues of the peptide recognized by KD-247 is replaced with other amino acid residues, peptides wherein each one of the amino acid residues in the sequence "IHIGPGRAFY" derived from HIV-1 (MN strain) was replaced with the other 19 naturally occurring amino acid residues were synthesized and reactivity of these peptides with KD-247 was measured as described above. As shown in FIG. 2, it was confirmed that only few other amino acid residues may be replaced for the middle portion sequence "PGR", especially the arginine (R) residue is an essential amino acid residue. For the amino acid residues other than "PGR", they could be replaced with many other amino acid residues.

From the results as described above, it was found that KD-247 basically recognized "IGPGR" sequence and could still recognize those amino acid sequences with replacement of an amino acid residue within "IGPGR" sequence and/or its vicinity.

Example 2

Analysis of Amino Acid Sequence Recognized by Anti-HIV Monoclonal Antibody Using Expressed Proteins The recognition site of KD-247 as confirmed in Example 1 was based on the observation of the reaction between the short peptides and said antibody. For assessing an antibody binding to an antigenic protein, however, steric influence needs be considered in addition to the amino acid sequence of the binding portion of the antigen. Thus, binding of KD-247 to an expressed protein containing V3 region was determined.

A gene containing HIV-1 V3 region was first amplified by nested PCR technique using as a template cDNAs obtained from HIV-1 RNA genes from plasma of patients infected with HIV-1 with a reverse transcriptase or HIV-1 proviral DNAs of peripheral blood mononuclear cells. Primers used for the first PCR were: 5'-ACACATGGAATTAGGCCAGT-3' (OA-4) (SEQ ID NO: 1) and 5'-AAATTCCCCTCCACAATTAA-3' (OD-4) (SEQ ID NO: 2), and primers used for the second PCR were: 5'-GCCGGATCCTCAACTCAACTGCTGTTAAAT-3' (EB-2) (SEQ ID NO: 3) and 5'-GCTCTGCAGTCAAATTTCTGGGTCCCCTCCTGAGG-3' (EC-2) (SEQ ID NO: 4). The amplified DNA fragments were purified, cleaved with restriction enzymes BamHI and PstI and cloned into vector plasmids (pUEXI) containing a β-galactosidase (β-Gal) gene. The resulting vectors were introduced into competent cells for cloning. PCR was performed using the cloned DNAs as a template and EB-2 and EC-2 primers and a nucleotide sequence of V3 region was analyzed using the amplified DNAs as a template and a DNA sequencer. Based on the obtained nucleotide sequence, an amino acid sequence of V3 region was determined.

On the other hand, each of the cloned *E. coli* cells where the genetic sequence was analyzed were cultured and a fusion protein of V3 region and a beta-galactosidase (V3/β-Gal) was obtained as described below. First, the cultured *E. coli* cells were disrupted with a cell-disrupting device, the disrupted cells were centrifuged, and the precipitates were dissolved in Tris buffer (pH7.5) containing 0.5% Triton X-100 followed by further centrifugation. The precipitates containing inclusion bodies were dissolved in Tris buffer (pH 7.5) containing 8M urea to purify V3/β-Gals. The obtained V3/β-Gals were subjected to SDS-PAGE so as to confirm that the fusion proteins were expressed with no abnormality. Then, ELISA was performed in order to adjust a concentration of V3/β-Gals. Using a plate with an immobilized anti-β-Gal antibody, either the expressed V3/β-Gals or commercially available p-Gal was added thereto. Peroxidase-labeled anti-p-Gal antibody was used as a detector antibody. A calibration curve was prepared with the results obtained from the standard and a concentration of the expressed V3/β-Gals was determined in terms of a concentration of β-Gal.

Then, in order to assess reactivity between V3/β-Gals and KD-247, additional ELISA was performed. Plates were immobilized with the anti-β-Gal antibody and were reacted with 200 ng/ml of each of V3/β-Gals. To the captured V3/β-Gals was reacted with 1 μg/ml of KD-247 and the reaction was detected with a peroxidase-labeled anti-human IgG antibody. Binding of KD-247 to each of V3/β-Gals was presented relative to the absorbance (100%) of a positive control as set in each of the plates, i.e. V3/β-Gal from HIV-1 MN strain.

FIG. 3 shows a relative binding activity of KD-247 to the amino acid sequences of the V3 middle portion of each of V3/β-Gals wherein about 120 sorts of HIV-1 clones from patients were analyzed. The clones that exhibited 100% or more of the relative binding had the amino acid sequences of the middle portion of V3 region: "IGPARAF" (SEQ ID NO: 5), "IGPGRSF" (SEQ ID NO: 6), "IGPGRAL" (SEQ ID NO: 7), "IGPGRTF" (SEQ ID NO: 8), "IGPGRAI" (SEQ ID NO: 9), "VGPGRAL" (SEQ ID NO: 10), and "IGPGRAF" (SEQ ID NO: 11). These sequences may be referred to as exemplary "reference sequences" for assessing fitness to KD-247.

Example 3

Analysis of Amino Acid Sequence of HIV-1 V3 Region and Viral Neutralizing Activity Correlation between the amino acid sequences of V3 region and the neutralizing activity was determined using laboratory strains and clinically isolated strains of HIV-1.

Nucleotide sequences of HIV-1 V3 region were determined as described in Example 2. The viruses were reacted with varied concentrations of KD-247 at 37° C. for 1 hour and then inoculated into peripheral blood mononuclear cells from healthy adults activated with phytohemagglutinin. After culture for 7 days, the cells were washed and a culture was further continued in the presence of IL-2 for 7 days. An amount of HIV-1 p24 antigen in the culture supernatant was measured by ELISA. The amount of p24 antigen obtained in the absence of the antibody was taken as 100% and each concentration of KD-247 added that reduced 50% ($IC_{50}$) or 90% ($IC_{90}$) of p24 antigen were presented as the neutralizing activity.

As shown in Table 1, the neutralizing activity of KD-247 was dependent upon the amino acid sequences in the middle portion of V3 region. Namely, all the HIV-1 viruses that had the "IGPGRAF" sequence in the middle portion of V3 region, binding of which sequence to KD-247 was confirmed in Examples 1 and 2, were neutralized by KD-247. This indicates that the amino acid sequences in the middle portion of V3 region have correlation with the binding activity and the neutralizing activity of KD-247 to said virus.

TABLE 1

| HIV-1 Strain | Amino acid sequence of V3 region | SEQ ID NO: | Neutralizing activity (μg/ml) IC$_{90}$ | IC$_{50}$ |
|---|---|---|---|---|
| Laboratory strain | | | | |
| MN | CTRPNYNKRKRIHIGPGRAFYTTKNIIGTIRQAHC | SEQ ID NO: 73 | 1 | 0.1 |
| IIIB | CTRPNNNTRKRKSIQRGPGRAFVTIGKIGNMRQAHC | SEQ ID NO: 74 | >50 | >50 |
| SF2 | CTRPNNNTRKGIHIGPGRAFYATEKIVGDIRQAHC | SEQ ID NO: 75 | 5 | 1 |
| AD8 | CTRPNNNTRKSIHIGPGRAFYTTGDIIGDIRQAHC | SEQ ID NO: 76 | 10 | 5 |
| 89.6 | CTRPNNNTRRRLSIGPGRAFYARRNIIGDIRQAHC | SEQ ID NO: 77 | 2.5 | 0.2 |
| Clinically isolated strain | | | | |
| 1 | CTRPNNNRRTRIHIGPGRAFYTTKNIIGTIRQAHC | SEQ ID NO: 78 | 5 | 0.3 |
| 2 | CTRPSNNKRKSIHIGPGRAFYTTKNIIGDIRQAHC | SEQ ID NO: 79 | 5 | 0.4 |
| 3 | CTRPNNNTRKSIHIGPGRAFYTTGEIIGDIRQAHC | SEQ ID NO: 80 | 8 | 0.6 |
| 4 | CTRPNNNTRKSIHMGPGKAFYTTGDIIGDIRQAHC | SEQ ID NO: 81 | >50 | >50 |
| 5 | CTRINNNTRKSIHIGPGRAFYATGEIIGNIKQAHC | SEQ ID NO: 82 | 10 | 1.4 |
| 6 | CTRPNNNTRKSIRIQRGPGRAFVTIGKIGNMRQAHC | SEQ ID NO: 83 | >50 | >50 |
| 7 | CIRPNNNTRKGIHILYWKKAIGGTNRQAHC | SEQ ID NO: 84 | >50 | >50 |
| 8 | CTRPNNNTRKSIRIQRGPGRAFVTIGKIINMIRQAHC | SEQ ID NO: 85 | >50 | >50 |
| 9 | CTGPNNNTRKSIRIQRGPGRAFVTIGKIGNMRQAHC | SEQ ID NO: 86 | >50 | >50 |
| 10 | CIRPNNNTRKGIHIGPGRAFYATDNIINTIRQAHC | SEQ ID NO: 87 | 8 | 1.2 |
| 11 | CTRPHKTIRKRIHIGPGRAFYTTKQIEGNIRQAHC | SEQ ID NO: 88 | 5 | 0.4 |
| 12 | CTRPSNNTRRRIHIGPGRAFYTTRQIRGDIRQAHC | SEQ ID NO: 89 | 4 | 0.2 |
| 13 | CTRPNNNIRKHIHIGPGRAFYTTRGIRDTIKQAHC | SEQ ID NO: 90 | 10 | 0.6 |
| 14 | CTRPNYNTRKGIHIGPGRAFVTTKGIRDTIKQAHC | SEQ ID NO: 91 | 4 | 0.3 |
| 15 | CTRPNNNTRKSILIGPGQWFYTGQNIIDTIRQAHC | SEQ ID NO: 92 | >50 | >50 |
| 16 | CTRPNNNTRKSIPLGPGQAWYTTGQILGDIRQAHC | SEQ ID NO: 93 | >50 | >50 |
| 17 | CTRPSNNTRTSITIGPGQVFYRTGDIIGDIRQAHC | SEQ ID NO: 94 | >50 | >50 |
| 18 | CTRPSNNTRTSITIGPGQVFYRTGDIIGDIRQAHC | SEQ ID NO: 95 | >50 | >50 |

Example 4

Analysis of Amino Acid Sequence of V3 Region in Clinical Sample And Test for Fitness of Patients to KD-247

A HIV-1 gene was analyzed from plasma or peripheral blood mononuclear cells from patients as described in Example 2. Based on this analysis, an amino acid sequence of HIV-1 V3 region was deduced and compared with "reference sequence", i.e. the amino acid sequences that were confirmed to be strongly reactive with KD-247 in Example 2, to test fitness of each of patients to KD-247.

Table 2 shows amino acid sequences deduced from the HIV-1 gene in plasma or peripheral blood mononuclear cells from patients and fitness of each of patients to KD-247. The amino acid sequences enclosed by the dotted line were compared with the "reference sequences" (SEQ ID NO: 5 to SEQ ID NO: 11) obtained in Example 2. When the amino acid of interest was consistent with one of the "reference sequences", it was assessed as being "fit" whereas when the amino acid of interest was not consistent with any one of the "reference sequences", it was assessed as being "unfit".

TABLE 2

| Patient No. | Amino acid sequence of V3 region | | | SEQ ID NO: | To be assessed |
|---|---|---|---|---|---|
| 1 | CTRPSNNTRKSIH | IGPGRAF | YTTGDIIGDIRQAHC | SEQ ID NO: 96 | Fit |
| 2 | CTRPNNHTRKSIH | MGARRAW | HTTGEIIGNLRQAHC | SEQ ID NO: 97 | Unfit |
| 3 | CTRPNNNTRKSIH | IGPGRAF | YATGEIVGDIRQAHC | SEQ ID NO: 98 | Fit |
| 4 | CTRPGNNTRKSIN | IGPGRAL | YATGDIVGNIRQAYC | SEQ ID NO: 99 | Fit |
| 5 | CTRPHNNTRKSIH | IGPGRAF | YATGEITGDIRRAHC | SEQ ID NO: 100 | Fit |
| 6 | CTRPNNNTRKRIS | MGPGRVY | YTTGQIIGDIRQAHC | SEQ ID NO: 101 | Unfit |
| 7 | CTRPHNNVRSRIH | IGPGRAF | YTTKRINGNIRQAYC | SEQ ID NO: 102 | Fit |
| 8 | CTRPSNNTSKSIS | IGPGRAI | YATGRIIGDIRQAHC | SEQ ID NO: 103 | Fit |
| 9 | CSRPSNNTRKGIH | IGPGRAF | FTTGEITGDIRQAHC | SEQ ID NO: 104 | Fit |
| 10 | CTRPNNNTRKSIH | MGPGKTF | YTTGGIIGNIRQAHC | SEQ ID NO: 105 | Unfit |
| 11 | CTRPNNNTRKSIN | IGPGRAF | YTTGEIIGDIRQAHC | SEQ ID NO: 106 | Fit |
| 12 | CTRPNNNTRKSIH | MGPGSVL | YATGAIVGNIRQAHC | SEQ ID NO: 107 | Unfit |
| 13 | CTRPNNNTRKSIH | IGPGRAF | YATGQIIGNIRQAHC | SEQ ID NO: 108 | Fit |
| 14 | CTRPNNNTRKSIH | IGPGRAF | YATGSIMGNIRQAHC | SEQ ID NO: 109 | Fit |
| 15 | CTRPNNNTRKGIH | VGPGRAL | YTT*EIIGNIRQAHC | SEQ ID NO: 110 | Fit |
| 16 | CTRPNNNTRKSIH | IGPGRAF | YATGQVIGDIRKAYC | SEQ ID NO: 11 | Fit |
| 17 | CTRPNNNTRKSIH | IGPGRAF | YTTGGIIGDIRQAYC | SEQ ID NO: 112 | Fit |
| 18 | CTRPSNNTRTSIT | IGPGQVF | YRTGDIIGDIRKAYC | SEQ ID NO: 113 | Unfit |

TABLE 2-continued

| Patient No. | Amino acid sequence of V3 region | | | SEQ ID NO: | To be assessed |
|---|---|---|---|---|---|
| 19 | CTRPNNNTRKGIH | IGPGRAF | YATGEIIGDIRQAHC | SEQ ID NO: 114 | Fit |
| 20 | CERPNNNTRKSIH | IGPGRAF | YAAGEIIGDIRQAHC | SEQ ID NO: 115 | Fit |
| 21 | CTRPNNNTRKSIH | VGPGRAL | Y*TTDIIGDIRQAHC | SEQ ID NO: 116 | Fit |
| 22 | CTRPNNNTRKSIH | IGPARAF | YTTGDIIGDIRQAHC | SEQ ID NO: 117 | Fit |
| 23 | CTRPNNNTRKGIN | IGPGRAF | YATGAIIGDVRKAHC | SEQ ID NO: 118 | Fit |
| 24 | CTRPSNNTGRGIR | IGPGRAF | YATQYITGDIRQAHC | SEQ ID NO: 119 | Fit |
| 25 | CTRPNHNIRKPIH | IGPGRSF | YTTGQIIGNIRQAHC | SEQ ID NO: 120 | Fit |
| 26 | CTRPNNNTRKRIT | LGPGRVY | YTTGQIIGNIRQAHC | SEQ ID NO: 121 | Unfit |
| 27 | CTRPNNNTRKSIH | IGPGRAL | YTT*DIIGDIRHAHC | SEQ ID NO: 122 | Fit |
| 28 | CTRPNNNTRKSIT | IGPGRAF | FTTGDTIGDIRKAYC | SEQ ID NO: 123 | Fit |
| 29 | CIRPNNNTRKSIH | IGPGRAF | FATDKITGDIRQAHC | SEQ ID NO: 124 | Fit |
| 30 | CARPNNNTRKSIH | IGPGRAF | YATEKIIGDIRQAHC | SEQ ID NO: 125 | Fit |
| 31 | CTRPNNNTRKGIH | IGPGRAF | YATGQIIGNIRQAHC | SEQ ID NO: 126 | Fit |
| 32 | CTRPNNNTRKSIH | IGPGRTF | YTTGDIIGDIRQAHY | SEQ ID NO: 127 | Fit |
| 33 | CTRPNNNTRKSIH | IGPGSAF | YTTGEIIGDIRQAHC | SEQ ID NO: 128 | Unfit |
| 34 | CTRPHNNTMKSIH | IGPGRAF | YATGQVIGDIRKAYC | SEQ ID NO: 129 | Fit |
| 35 | CARPNNNTRKSIT | IGPGRAF | YTTGEIIGDIRQAHC | SEQ ID NO: 130 | Fit |

*: Deletion of amino acid residue

The invention claimed is:

1. A method for enhancing the efficacy of a monoclonal antibody preparation, wherein said monoclonal antibody is an antibody recognizing the V3 region of the envelope glycoprotein gp120 of human immunodeficiency virus type1 (HIV-1), the method comprising:
   a. isolating a nucleotide sequence of a gene of a target molecule from a patient and deducing the amino acid sequence encoded by the nucleotide sequence;
   b. comparing the deduced amino acid sequence with a reference amino acid sequence having a specific epitope recognized by a monoclonal antibody comprised by said monoclonal antibody preparation to determine if the deduced amino acid sequence shares the specific epitope with the reference amino acid sequence to determine if the monoclonal antibody will recognize the deduced amino acid sequence; and
   c. administering the monoclonal antibody preparation to patients in which the deduced amino acid sequence shares a specific epitope with the reference amino acid sequence so that the monoclonal antibody can recognize the deduced amino acid sequence.

2. The method according to claim 1, wherein comparing the deduced amino acid sequence and the reference amino acid sequence is conducted using as an index the binding of said monoclonal antibody to a peptide or an expressed protein having the deduced amino acid sequence and/or biological activities of said monoclonal antibody.

3. The method according to claim 1, wherein the reference amino acid sequence of HIV-1 is selected from the group consisting of IGPARAF (SEQ ID NO:5), IGPGRSF (SEQ ID NO:6), IGPGRAL (SEQ ID NO:7), IGPGRTF (SEQ ID NO:8), IGPGRAI (SEQ ID NO:9), VGPGRAL (SEQ ID NO:10), and IGPGRAF (SEQ ID NO:11).

* * * * *

UNITED STATES PATENT AND TRADEMARK OFFICE
CERTIFICATE OF CORRECTION

| | | |
|---|---|---|
| PATENT NO. | : 8,332,159 B2 | Page 1 of 1 |
| APPLICATION NO. | : 10/546293 | |
| DATED | : December 11, 2012 | |
| INVENTOR(S) | : Murakami et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this
Twenty-third Day of September, 2014

Michelle K. Lee
*Deputy Director of the United States Patent and Trademark Office*